United States Patent [19]
Hao et al.

[11] Patent Number: 5,591,865
[45] Date of Patent: Jan. 7, 1997

[54] CRYSTAL MODIFICATION OF A DIKETOPYRROLOPYRROLE PIGMENT

[75] Inventors: Zhimin Hao, Marly; Abul Iqbal, Arconciel; Fritz Herren, Düdingen, all of Switzerland

[73] Assignee: Ciba-Geigy Corporation, Tarrytown, N.Y.

[21] Appl. No.: 493,853

[22] Filed: Jun. 22, 1995

[30] Foreign Application Priority Data

Jun. 29, 1994 [CH] Switzerland .................... 2074/94

[51] Int. Cl.$^6$ .................................................. C07D 487/04
[52] U.S. Cl. ............................................................ 548/453
[58] Field of Search .............................................. 548/453

[56] References Cited

U.S. PATENT DOCUMENTS

| | | | |
|---|---|---|---|
| 4,415,685 | 11/1983 | Iqbal et al. | 524/92 |
| 4,579,949 | 4/1986 | Rochat et al. | 546/167 |

FOREIGN PATENT DOCUMENTS

| | | |
|---|---|---|
| 0061426 | 9/1982 | European Pat. Off. . |
| 0094911 | 11/1983 | European Pat. Off. . |

OTHER PUBLICATIONS

J. Mizuguchi et al., Acta Crystallographica, vol. B48, Part 5, pp. 696–700, (1992).
H. Langhals et al., Angewandte Chemie, vol. 101, Nr. 4, pp. 497–499, (1989).
W. Herbst, K. Hunger: Industrial Organic Pigments pp. 41–43, pp. 427–428 & 453–454 (1993).

*Primary Examiner*—David B. Springer
*Attorney, Agent, or Firm*—Michele A. Kovaleski

[57] ABSTRACT

Diketopyrrolopyrrole of the formula (I)

in its β-modification.

The new β-modification is suitable as a pigment for coloring high-molecular weight organic material and shows, in comparison to the α-modification, a shift in shade towards yellowish-red.

8 Claims, No Drawings

CRYSTAL MODIFICATION OF A DIKETOPYRROLOPYRROLE PIGMENT

The present application relates to a new crystal modification of 1,4-diketo-3,6-bis(3-chlorophenyl)pyrrolo[3,4-c]pyrrole, to its preparation and the use of this new product as a pigment.

It is general knowledge that a number of representatives of different classes of organic pigments are polymorphous. Despite having the same chemical composition, such pigments occur in two or more crystal modifications. This is the case in particular for phthalocyanine, quinacridone and some azo pigments (cf. e.g. W. Herbst, K. Hunger, Industrial Organic Pigments (1993), 41–43, 427–428, 453–454). For some other pigments, in contrast, only one single crystal modification is known. For instance, despite a number of attempts it has hitherto been impossible to obtain, for any one of the diketopyrrolopyrrole pigments, which have been known for some years and are described, for example, in U.S. Pat. Nos. 4,415,685 and 4,579,949, a second crystal modification.

It has recently been found that leaving groups, for example those of the formula

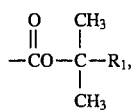

in which $R_1$ is $C_1$–$C_6$alkyl, can be introduced readily even into insoluble substances, like the diketopyrrolopyrrole pigments, with formation of soluble carbamates having the basic structure

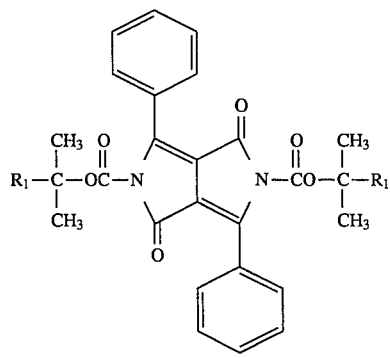

and that, by thermal (heating to temperatures of between 50° and 400° C.), chemical (with organic or inorganic acids or bases) or photolyric (exposure with, for example, wavelengths below 375 nm) treatment the original pigment can be reformed. These studies are described in parallel patent applications (application date October 1993).

Astonishingly it has now been found that, in the case of the diketopyrrolopyrrole of the formula

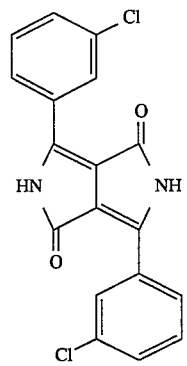

the abovementioned reformation of the (N-unsubstituted) pigment by chemical treatment under specific conditions leads not to the previously known modification but to a new crystal modification. The new modification, referred to hereinafter as the β-modification, differs from the known modification, referred to hereinafter as the α-modification, by a specific, different X-ray diffraction pattern, but also by a shift in shade towards yellowish-red, which shift is of interest for the utility as a pigment.

The complete X-ray diffraction pattern are determined by conventional methods using a Siemens D500® X-ray diffractometer (CuK$_\alpha$ radiation).

The X-ray diffraction pattern of the less yellowish known α-modification is characterized by the following diffraction lines

| Interplanar spacings (d values in Å) | double glancing angle (2 Θ) | relative intensity |
|---|---|---|
| 14.2895 | 6.18 | 32 |
| 7.1039 | 12.45 | 14 |
| 6.7517 | 13.10 | 53 |
| 5.7301 | 15.45 | 9 |
| 5.3610 | 16.52 | 29 |
| 4.7321 | 18.74 | 41 |
| 4.2189 | 21.04 | 44 |
| 3.7282 | 23.85 | 11 |
| 3.4883 | 25.52 | 62 |
| 3.3796 | 26.35 | 37 |
| 3.2458 | 27.46 | 100 |
| 3.1650 | 28.17 | 24 |
| 2.9888 | 29.87 | 24 |

The present invention relates to the diketopyrrolopyrrole of the formula

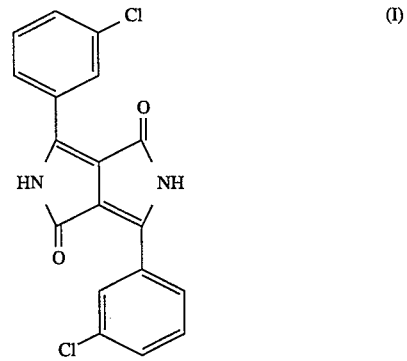

(I)

in its β-modification, whose X-ray diffraction pattern is characterized by the following diffraction lines

| Interplanar spacings (d values in Å) | double glancing angle (2 Θ) | relative intensity |
|---|---|---|
| 13.1801 | 6.70 | 100 |
| 6.6594 | 13.29 | 50 |
| 6.3830 | 13.86 | 91 |
| 5.7056 | 15.52 | 40 |
| 5.1298 | 17.27 | 54 |
| 4.5362 | 19.55 | 47 |
| 4.4159 | 20.09 | 36 |
| 4.0577 | 21.89 | 29 |
| 3.3910 | 26.26 | 25 |
| 3.1307 | 28.49 | 22 |

This new β-modification is prepared by dissolving a soluble diketopyrrolopyrrole of the formula

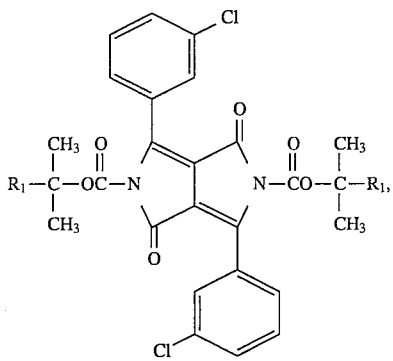

(II)

in which $R_1$ is $C_1$–$C_6$alkyl, in water and/or an organic solvent, heating the solution at a temperature of between 50° and 150° C. in the presence of an acid, and then isolating the product, which has precipitated after cooling, by conventional methods.

$R_1$ as $C_1$–$C_6$alkyl is for example methyl, ethyl, n-propyl, isopropyl, n-butyl, tert-butyl, n-amyl or hexyl.

$R_1$ is preferably ethyl, but especially methyl.

The dissolved diketopyrrolopyrrole of the formula II is advantageously treated in the presence of the acid under reflux for from 5 to 30 minutes at 70° to 130° C., depending on the solvent, and the mixture is then advantageously cooled to from 10° to 30° C.

Solvents which can be used are water or inert aprotic organic solvents, for example dimethylformamide, tetrahydrofuran, ethylene glycol, ethylene glycol monomethyl ether, dodecane, toluene, xylene, acetylacetone, dimethyl sulfoxide or mixtures thereof. Preference is given to tetrahydrofuran, xylene or in particular toluene.

Suitable acids are both inorganic and organic acids, for example hydrochloric acid, sulfuric acid, toluenesulfonic acid or trifluoroacetic acid. 4-Toluenesulfonic acid is preferred. It is advantageous to employ from 10 to 30, preferably from 15 to 25 mol, of acid per mole of diketopyrrolopyrrole of the formula II. The acid can be added either before, together with or after the pigment salt suspension, preferably before or together with the pigment salt suspension.

It is preferred to use from 15 to 20 mol of 4-toluenesulfonic acid, based on the diketopyrrolopyrrole, in toluene at from 80° to 110° C. for from 10 to 20 minutes.

Diketopyrrolopyrroles of the formula II can be obtained in analogy to generally known methods, for example by reacting a diketopyrrolopyrrole of the formula I with a dicarbonate of the formula

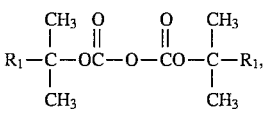

(III)

or with a trihaloacetic ester of the formula

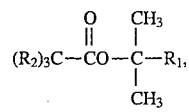

(IV)

in which $R_2$ is chlorine, fluorine or bromine, or with an azide of the formula

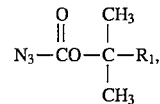

(V)

$R_1$ being in each case as defined above, in an aprotic organic solvent in the presence of a base as catalyst at temperatures of between 0° and 400° C. for from 2 to 80 hours.

The dicarbonate of the formula III, the trihaloacetic ester of the formula IV or the azide of the formula V is advantageously employed in a from 2- to 10-fold excess.

The diketopyrrolopyrrole of the formula I is preferably reacted with a dicarbonate of the formula III.

Dicarbonates of the formula III, trihaloacetic esters of the formula IV and azides of the formula V are known substances. Any that may be novel can be prepared in analogy to generally known methods.

Examples of suitable solvents are ethers, such as tetrahydrofuran or dioxane, or glycol ethers, such as ethylene glycol methyl ether, ethylene glycol ethyl ether, diethylene glycol monomethyl ether or diethylene glycol monoethyl ether, dipolar aprotic solvents, such as acetonitrile, benzonitrile, N,N-dimethylformamide, N,N-dimethylacetamide, nitrobenzene or N-methylpyrrolidone, halogenated aliphatic or aromatic hydrocarbons, such as trichloroethane, benzene or alkyl-, alkoxy- or halogen-substituted benzene, such as toluene, xylene, anisole or chlorbenzene, or aromatic nitrogen heterocycles, such as pyridine, picoline or quinoline. Examples of preferred solvents are tetrahydrofuran, N,N-dimethylformamide and N-methylpyrrolidone. The solvents mentioned may also be employed as mixtures. It is advantageous to use from 5 to 20 parts by weight of solvent per part by weight of the reactants.

Examples of bases which are suitable as catalysts are the alkali metals themselves, such as lithium, sodium or potassium and their hydroxides or carbonates, or alkali metal amides, such as lithium amide, sodium amide or potassium amide, or alkali metal hydrides, such as lithium hydride, sodium hydride or potassium hydride, or alkaline earth metal or alkali metal alcoholates which are derived, in particular, from primary, secondary or tertiary aliphatic alcohols of 1 to 10 carbon atoms, for example lithium, sodium or potassium methylate, ethylate, n-propylate, isopropylate, n-butylate, sec-butylate, ten-butylate, 2-methyl-2-butylate, 2-methyl-2-pentylate, 3-methyl-3-pentylate or 3-ethyl-3-pentylate, and also organic aliphatic, aromatic or heterocyclic nitrogen bases, including for example diazabicyclooctane, diazabicycloundecene and 4-dimethylaminopyridine, and trialkylamines, for example trimethylamine or triethylamine. It is also possible to use a mixture of the bases mentioned.

Preference is given to the organic nitrogen bases such as, for example, diazabicyclooctane, diazabicycloundecene and, in particular, 4-dimethylaminopyridine.

The reaction is preferably carried out at-temperatures of between 10° and 100° C., in particular between 14° and 40° C., and at atmospheric pressure.

The β-diketopyrrolopyrrole of the invention is also suitable, as already described, for example in U.S. Pat. Nos. 4,415,685 and 4,579,949 for its α-modification, as a pigment for colouring high molecular weight organic material. However, it is transformed again into the α-modification on heating at temperatures which vary depending on the substrate, its use in materials which are processed at relatively high temperatures requires caution to be exercised.

Like many other pigments, the β-diketopyrrolopyrrole according to the invention can also be advantageously surface-treated by known methods in order to improve its properties in coating systems. Additives which are employed to reduce or avoid flocculation and to improve the dispersion stability can be used advantageously with the pigment according to the invention. The pigment treated in this way exhibits good properties, alone or mixed with other pigments, for the production of red masstone colorations in a variety of coating systems, but preferably in automotive finishing systems of the acrylic, alkyd and polyester type. 2-Phthalimidomethylquinacridone, quinacridonesulfonic acid and other similar derivatives are examples of deflocculating agents which can be used. In certain systems, the addition of polymeric dispersants may bring about an additional improvement in the properties of the pigment.

The β-diketopyrrolopyrrole according to the invention is employed in quantities of from 0.01 to 30% by weight, preferably from 0.1 to 10% by weight, based on the high molecular weight organic material to be coloured, and is incorporated into this material advantageously at temperatures between 20° and 180° C.

The β-diketopyrrolopyrrole according to the invention can be employed, for example, as a powder, paste, flush paste or formulation and is suitable, for example, for printing inks, sizing colours, binder colours or coatings of all kinds, such as physically and oxidatively drying coating materials, acid-, amine- and peroxide-curing coating materials or polyurethane coating materials. When the processing temperature permits it, the pigment can also be used for colouring synthetic, semisynthetic or natural macromolecular substances, alone or together with other organic or inorganic pigments. The resulting colorations, for example in coating materials, prints or plastics, are distinguished by a yellowish-red colour, good fastness to overspraying, migration, light and weathering, and by high tinctorial strength and transparency.

The pigment according to the invention can be used for colouring solid, elastic, pastelike, high-viscosity, low-viscosity or thixotropic materials and can be incorporated into these materials by methods which are known per se. For example, water-containing pastes can be obtained by stirring the pigment into water, with or without the addition of a wetting agent or dispersant, or by stirring or kneading the pigment into a dispersant in the presence of water and in the presence or absence of organic solvents or oils. These pastes can be employed in turn, for example, to produce flush pastes, printing inks, sizing colours and polymer dispersions. However, the pigment can also be introduced by stirring, rolling, kneading or grinding into water, organic solvents, non-drying oils, drying oils, coating materials, plastics or rubber. Finally, it is also possible to process the pigment by dry mixing with organic or inorganic materials, granules, fibrous substances, powders and other pigments, to give compositions.

The examples which follow illustrate the invention.

EXAMPLE 1a (Preparation of the Soluble Diketopyrrolopyrrole)

2.44 g of 4-dimethylaminopyridine and then 38.5 g of di-tert-butyl dicarbonate are added to a suspension of 28.6 g of 1,4-diketo-3,6-di(3-chlorophenyl)pyrrolo[3,4-c]pyrrole in 800 ml of tetrahydrofuran (dried over molecular sieve). The reaction mixture is stirred at room temperature for 24 hours with the exclusion of atmospheric moisture. The solvent is then distilled off under reduced pressure. The residue is washed with methanol and is dried in vacuo at room temperature, to give 38.6 g (86.5% of theory) of a bright orange product of the formula

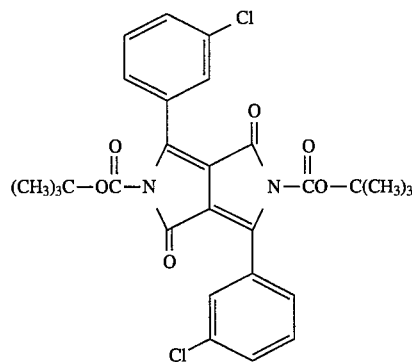

| Analysis: | C | H | N | Cl |
|---|---|---|---|---|
| calc.: | 60.33% | 4.70% | 5.03% | 12.72% |
| found: | 60.23% | 4.82% | 5.08% | 13.06% | b) 6.8 g of 4-toluenesulfonic acid are added to a mixture of 1.0 g of the product from a) and 75 ml of toluene. The reaction mixture is heated to 105° C., stirred vigorously at this temperature for 15 minutes, and then cooled suddenly in an ice bath to 20° C. The precipitated pigment is filtered off, washed with methanol and then with water, and dried in a vacuum drying cabinet,to give 0.56 g (57.2% of theory) of a red powder. MS(DEI): m/z 356 (M$^+$).

The X-ray diffraction pattern is characterized by the following diffraction lines

| Interplanar spacing (d values in Å) | double glancing angle (2 Θ) | relative intensity |
|---|---|---|
| 13.1801 | 6.70 | 100 |
| 6.6594 | 13.29 | 50 |
| 6.3830 | 13.86 | 91 |
| 5.7056 | 15.52 | 40 |
| 5.1298 | 17.27 | 54 |
| 4.5362 | 19.55 | 47 |
| 4.4159 | 20.09 | 36 |
| 4.0577 | 21.89 | 29 |
| 3.3910 | 26.26 | 25 |
| 3.1307 | 28.49 | 22 |

EXAMPLE 2

7.5 g of the pigment whose preparation is described in Example 1b, 98.9 g of CAB solution comprising

| 41.00 g | of cellulose acetobutyrate ® CAB 531.1, 20% in 2:1 butanol/xylene (Eastman Chem.) |
| 1.50 g | of zirconium octoate |
| 18.50 g | of ® SOLVESSO 150* |
| 21.50 g | of butyl acetate and |
| 17.50 g | of xylene |

36.50 g of polyester resin ®DINAPOL H700 (Dynamit Nobel), 4.60 g of melamine resin ®MAPRENAL MF650 (Hoechst) and 2.50 g of dispersant ®DISPERBYK 160 (Byk Chemie) are dispersed together for 90 minutes using a shaker machine (total coating material 150 g, 5% pigment).

27.69 g of the masstone coating material obtained in this way are mixed, for the basecoat finish, with 17.31 g of Al stock solution (8% strength) comprising

| | |
|---|---|
| 12.65 g | of ® SILBERLINE SS 3334AR, 60% (Silberline Ltd.) |
| 56.33 g | of CAB solution (as composition above) |
| 20.81 g | of polyester resin ® DINAPOL H700 |
| 2.60 g | of melamine resin ® MAPRENAL MF650 and |
| 7.59 g | of ® SOLVESSO 150* | and the mixture is applied by spraying (wet film thickness about 20 μm) to an aluminium panel. After an evaporation time of 30 minutes at room temperature, a thermosetting acrylic varnish comprising

| | |
|---|---|
| 29.60 g | of acrylic resin ® URACRON 2263 XB, 50% in xylene/butanol (Chem. Fabrik Schweizerhalle), |
| 5.80 g | of melamine resin ® CYMEL 327, 90% in isobutanol, |
| 2.75 g | of butylglycol acetate, |
| 5.70 g | of xylene, |
| 1.65 g | of n-butanol, |
| 0.50 g | of silicone oil, 1% in xylene, |
| 3.00 g | of light stabilizer ® TINUVIN 900, 10% in xylene (Ciba), and |
| 1.00 g | of light stabilizer ® TINUVIN 292, 10% in xylene (Ciba) | is applied (wet film thickness about 50 μm) by spraying as a topcoat finish. After evaporation at room temperature for a further 30 minutes the coating is baked at 130° C. for 30 minutes.

EXAMPLE 3

0.6 g of the pigment prepared according to Example 1b is mixed with 67 g of polyvinyl chloride, 33 g of dioctyl phthalate, 2 g of dibutyltin dilaurate and 2 g of titanium dioxide and the mixture is processed on a roller mill at 160° C. for 15 minutes to give a thin sheet. The red PVC sheet produced in this way is distinguished by very good fastness properties.

What is claimed is:

1. A diketopyrrolopyrrole of the formula

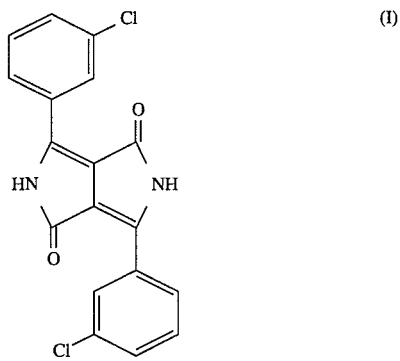

(I)

in its β-modification, whose X-ray diffraction pattern is characterized by the following diffraction lines

| Interplanar spacings (d values in Å) | double glancing angle (2 Θ) | relative intensity |
|---|---|---|
| 13.1801 | 6.70 | 100 |
| 6.6594 | 13.29 | 50 |
| 6.3830 | 13.86 | 91 |
| 5.7056 | 15.52 | 40 |
| 5.1298 | 17.27 | 54 |
| 4.5362 | 19.55 | 47 |
| 4.4159 | 20.09 | 36 |
| 4.0577 | 21.89 | 29 |
| 3.3910 | 26.26 | 25 |
| 3.1307 | 28.49 | 22. |

2. A process for the preparation of a diketopyrrolopyrrole according to claim 1, which comprises dissolving a soluble diketopyrrolopyrrole of the formula

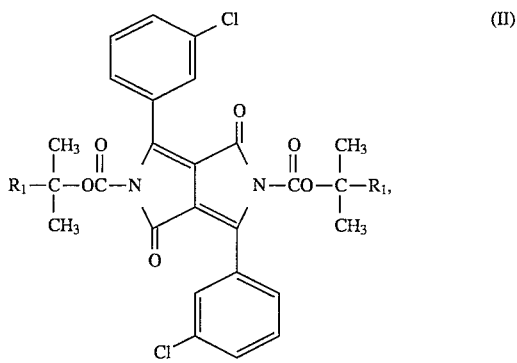

(II)

in which $R_1$ is $C_1$–$C_6$alkyl, in water or an organic solvent with or without water, heating the solution at a temperature of between 50° and 150° C. in the presence of an acid, and then isolating the product, which has precipitated after cooling, by conventional methods.

3. A process according to claim 2, wherein a compound of the formula II is used in which $R_1$ is ethyl or, preferably, methyl.

4. A process according to claim 2, wherein the diketopyrrolopyrrole of the formula II is treated at 70° to 130° C. for from 5 to 30 minutes and the mixture is then cooled to from 10° to 30° C.

5. A process according to claim 2, wherein the solvent used is tetrahydrofuran, xylene or toluene.

6. A process according to claim 2, wherein the acid used is 4-toluenesulfonic acid.

7. A process according to claim 2, wherein from 10 to 30 mol of acid are employed per mole of diketopyrrolopyrrole of the formula II.

8. A process according to claim 2, wherein the diketopyrrolopyrrole of the formula II is treated with from 15 to 20 mol of 4-toluenesulfonic acid, based on the diketopyrrolopyrrole, in toluene at 80° to 110° C. for from 10 to 20 minutes.

* * * * *